United States Patent
Reilly

(10) Patent No.: US 9,980,491 B2
(45) Date of Patent: May 29, 2018

(54) PROBIOTIC COMPOSITIONS AND METHODS OF USE

(71) Applicant: Siobhan Reilly, Ponca City, OK (US)

(72) Inventor: Siobhan Reilly, Ponca City, OK (US)

( * ) Notice: Subject to any disclaimer, the term of this patent is extended or adjusted under 35 U.S.C. 154(b) by 0 days. days.

(21) Appl. No.: 14/809,173

(22) Filed: Jul. 25, 2015

(65) Prior Publication Data

US 2017/0020137 A1    Jan. 26, 2017

(51) Int. Cl.
*A01N 63/00*     (2006.01)
*C12R 1/01*     (2006.01)

(52) U.S. Cl.
CPC .................................. *A01N 63/00* (2013.01)

(58) Field of Classification Search
None
See application file for complete search history.

(56) References Cited

U.S. PATENT DOCUMENTS

| | | |
|---|---|---|
| 7,575,744 B2 | 8/2009 | Doyle et al. |
| 8,685,697 B1 | 4/2014 | Pasternack et al. |
| 2012/0107291 A1 * | 5/2012 | Burcelin ............... A23L 1/3014 424/93.45 |
| 2014/0186409 A1 * | 7/2014 | Lang ..................... A61K 8/99 424/400 |
| 2014/0341872 A1 * | 11/2014 | Ware ..................... A23L 3/3571 424/93.45 |

OTHER PUBLICATIONS

Fayol-Messaoudi et al., "pH-, Lactic Acid-, and Non-Lactic Acid-Dependent Activities of Probiotic Lactobacilli against *Salmonella enterica* Serovar Typhimurium", Applied and Environmental Microbiology 2005, vol. 71, pp. 6008-6013.*
Ouali et al., "Identification of lactobacilli with inhibitory effect on biofilm formation by pathogenic bacteria on stainless steel surfaces", International Journal of Food Microbiology, vol. 191, pp. 116-124.*
Fracchia, L., et al., "A Lactobacillus-derived biosurfactant inhibits biofilm formation of human pathogenic Candida albicans biofilm producers," Current Research, Technology and Education Topics in Applied Microbiology and Microbial Biotechnology, 2010, pp. 827-837.
Ku, S., et al., "Enhancement of Anti-tumorigenic Polysaccharide Production, Adhesion, and Branch Formation of Bifidobacterium bifidum BGN4 by Phytic Acid," Food Sci. Biotechnol. vol. 18, No. 3, 2009.
Rendueles, O., et al., "Multi-species biofilms: how to avoid unfriendly neighbors," FEMS Microbiol Rev 36 (2012) 972-989.

* cited by examiner

*Primary Examiner* — Michelle F. Paguio Frising
(74) *Attorney, Agent, or Firm* — Bethany J. Whelan

(57) ABSTRACT

A probiotic composition and methods for the mitigation, inhibition, and/or exclusion of microorganisms.

17 Claims, 1 Drawing Sheet

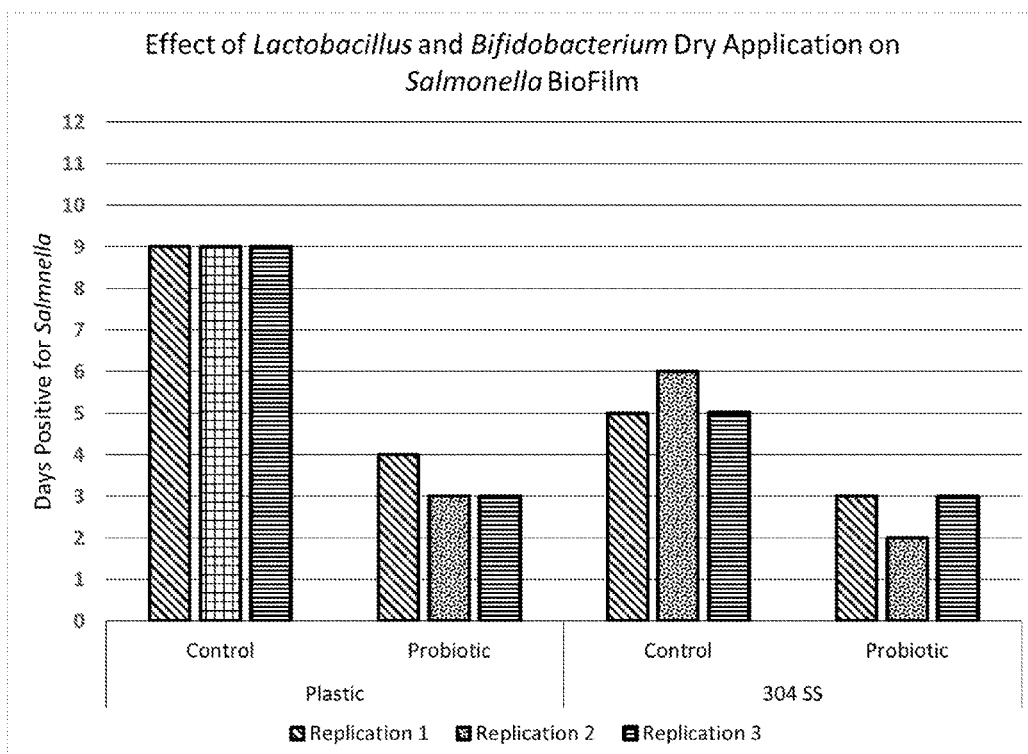

PROBIOTIC COMPOSITIONS AND METHODS OF USE

TECHNICAL FIELD

The present disclosure provides probiotic compositions for use in food processing facilities or on a food product. Further provided are methods for controlling pathogens in food processing facilities by utilizing the probiotic compositions disclosed herein.

BACKGROUND

The control of contamination by microorganisms is a recognized problem in the food processing industry. The process of preparing food products is largely concerned with preventing the contamination of such food products with harmful microorganisms. Indeed, many food processing facilities include equipment that is essentially closed to the external environment, difficult or impossible to clean and sanitize thus, hosting harmful microorganisms which can contaminate and/or colonize certain food product surfaces located in food processing equipment.

Indeed, in certain food processing facilities, pathogens may colonize food product surfaces and may cause food poisoning if cross contamination takes place. Furthermore, the colonization of certain pathogens may be detected during routine testing and screening of the food or the food production facility and can cause the company or the government to effectively shut down operations and and/or recall product from the market. Even worse, if consumers are exposed to the food containing the pathogen sickness or even death may occur.

Some types of bacteria can produce a substance that protects them from their environment and helps them to stick to food equipment surfaces. These bacterial congregations are known as biofilms. Many bacterial biofilms are ubiquitous in nature, and the food industry cannot escape many problems caused by pathogenic bacterial biofilms. Indeed, biofilms formed on food-processing equipment and other food product contact surfaces may act as a persistent source of contamination threatening the microbiological quality and safety of food products, and may further result in food-borne disease and economic losses. If it is a pathogenic microorganism that develops the biofilm on a food equipment surface, which cannot be easily seen, detected or removed, it can eventually break off or become dislodged during production or cleaning and contaminate food products or other food contact equipment. Interfering or preventing this from occurring is crucial to producing a safe and wholesome food product.

While many products are used to clean, i.e. a detergent or surfactant, and sanitize, i.e. a lethal agent or sanitizer such as chlorine, iodine, quaternary ammonia, peroxy compounds or chlorine dioxide, they are also difficult to use, mix, and apply to certain food processing equipment. Further, if these chemicals are improperly used they may not work or may impart a chemical hazard to the food product. Additionally, sanitizers like chlorine, iodine, quaternary ammonia, peroxy compounds or chlorine are corrosive to the food processing equipment and toxic to food production employees who utilize them to clean certain equipment. Moreover, if used at inappropriate concentrations on food contact surfaces; these chemicals can contaminate the food product such that the food product causes illness when ingested.

Furthermore, detergents and sanitizers are costly and may impart undesirable organoleptic changes in the food. Typically, a detergent must be applied before a sanitizer in order to be effective at removing and killing pathogens. Indeed, conventionally a detergent or surfactant must be applied to remove the biofilm before the pathogens can be killed. The procedure of applying detergents and sanitizers to clean effectively cannot be done if the target area cannot be reached. In the food processing industry, there are many surfaces that cannot be reached by current conventional methods and, thus, cannot be cleaned or sanitized.

As such, provided herein are probiotic compositions and methods of use for controlling pathogen growth in food processing facilities, for example on food product contact surfaces in food processing facilities. Further provided are probiotic compositions and methods for controlling pathogen growth on food product contact surfaces that eliminate food product contamination by pathogens that have not been effectively removed or by chemicals, such as detergents and sanitizers, used to clean food processing equipment. Furthermore, use of the probiotic compositions disclosed herein are not hazardous to food production equipment, employees, or the food product.

BRIEF SUMMARY OF THE INVENTION

The disclosure is directed, in one embodiment, to a probiotic composition having a population of microorganisms. In some embodiments, the probiotic composition includes an antiadhesion-producing microorganism, a biosurfactant-producing microorganism, and/or a biofilm producing microorganism. In certain embodiments, the probiotic composition includes species from the genus *Lactobacillus*, species from the genus *Bifidobacterium*, and combinations thereof.

In some embodiments, the probiotic composition degrades pathogenic biofilm. In certain embodiments, the probiotic composition is capable of mitigating pathogenic biofilm on a food product contact surface that may not be reachable via other detergents and sanitizers.

In some embodiments, the probiotic composition inhibits the growth of certain pathogenic microorganisms on the food product contact surfaces of food manufacturing equipment.

In certain embodiments, the probiotic composition is formulated as an aerosol composition. Accordingly, the application of the probiotic composition in aerosol form ensures that the probiotic composition is able to adequately coat all angles of the food product surface including those surfaces that are not reachable using conventional detergents and sanitizers.

Further, provided herein are methods for treating the food product contact surface of the food processing equipment in a food processing facility that includes disposing the probiotic composition(s) disclosed herein on the food product contact surface of the food processing equipment. In some embodiments, provided are methods for inhibiting the growth of pathogens, for example *Salmonella* spp, on food product contact surfaces. In some embodiments, provided are methods directed to the competitive exclusion of pathogens on a food product contact surface that comprises disposing the probiotic composition(s) disclosed herein on the food product contact surface.

Also provided are methods for mitigating pathogenic biofilm and the pathogens associated thereon from a food product contact surface via applying the probiotic compositions disclosed herein.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE DRAWINGS

FIG. 1 illustrates the effect of *Lactobacillus* and *Bifidobacterium* as a dry application on *Salmonella* biofilm.

DETAILED DESCRIPTION

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

As used herein the term "biosurfactant-producing microorganism" refers to a any microorganism capable of producing a biosurfactant. Non-limiting examples of biosurfactant-producing microorganisms may be from the genus *Lactobacillus* for example *Lactobacillus acidophilus, Lactobacillus casei, Lactobacillus paracasei, Lactobacillus fermentum, Lactobacillus lactis, Lactobacillus reuterii, Lactobacillus rhamnoses, Lactobacillus bulgaricus, Lactobacillus plantarum, Lactobacillus salivarius, Lactobacillus delbrueckii, Lactobacillus helveticus, Lactobacillus brevis, Lactobacillus sakei, Lactobacillus johnsonii*, and combinations thereof.

As used herein the term "antiadhesion-producing microorganism" refers to a any microorganism capable of producing a composition, for example an exopolysachharide, that contributes to disabling a pathogen's ability to adhere to a surface and/or produce biofilm, or can unglue a biofilm. Non-limiting examples of antiadhesion-producing microorganisms may be from the genus *Lactobacillus* and *Bifidobacterium* for example. For example, the antiadhesion-producing microorganism may be selected from, but are not limited to, the following: *Lactobacillus acidophilus, Lactobacillus casei, Lactobacillus paracasei, Lactobacillus fermentum, Lactobacillus lactis, Lactobacillus reuterii, Lactobacillus rhamnoses, Lactobacillus bulgaricus, Lactobacillus plantarum, Lactobacillus salivarius, Lactobacillus delbrueckii, Lactobacillus helveticus, Lactobacillus brevis, Lactobacillus sakei, Lactobacillus johnsonii, Bifidobacterium longum, Bifidobacterium bifidum, Bifidobacterium breve, Bifidobacterium infantis, Bifidobacterium adolecentis, Bifidobacterium lactis, Bidobacterium animalis, Enterococcus faecium*, and combinations thereof.

As used herein the term "biofilm producing microorganism" refers to a any microorganism capable of producing a biofilm. Non-limiting examples of biofilm-producing microorganisms may be from the genus *Bifidobaterium* and *Lactobacillus* for example, *Bifidobacterium longum, Bifidobacterium bifidum, Bifidobacterium breve, Bifidobacterium infantis, Bifidobacterium adolecentis, Bifidobacterium lactis, Bidobacterium animalis, Lactobacillus acidophilus, Lactobacillus casei, Lactobacillus paracasei, Lactobacillus fermentum, Lactobacillus lactis, Lactobacillus reuterii, Lactobacillus rhamnoses, Lactobacillus bulgaricus, Lactobacillus plantarum, Lactobacillus salivarius, Lactobacillus delbrueckii, Lactobacillus helveticus, Lactobacillus brevis, Lactobacillus sakei, Lactobacillus johnsonii*, and combinations thereof.

As used herein, the term "biofilm" refers to a matrix that is unique to each microorganism but has generalities within genera that is structural. For example, certain biofilms may comprise carbohydrates, proteins, nucleic acids, extracellular polymeric substances, and other components. Biofilms are capable of facilitating gene regulation for communication, defense, and growth of said microorganism.

As used herein, the term "pathogen" refers to an agent having the capability of producing a disease. For example, a pathogen may refer to a virus, bacterium, or other disease-producing microorganism. For example, the term pathogen may refer to any of the following: *Salmonella enterica, Salmonella salamae, Salmonella diarizonae, Salmonella houtenae, Salmonella indica, Salmonella bongori*, Enterotoxigenic *E. coli* (ETEC), Enteropathogenic *E. coli* (EPEC), Enteroinvasive *E. coli* (EIEC), Enterohemorrhagic *E. coli* (EHEC), Uropathogenic *E. coli* (UPEC), *Escherichia coli, Shigella*, and/or *Listeria*.

As used herein, the term "food product contact surface" is any surface that comes into contact with any ingredient incorporated into a finished food product.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

In some embodiments the probiotic composition includes one or more probiotics selected from *Lactobacillus acidophilus, Lactobacillus casei, Lactobacillus fermentum, Lactobacillus lactis, Lactobacillus reuterii, Lactobacillus bulgaricus, Lactobacillus plantarium, Lactobacillus salivarius, Bifidobacterium longum, Bifidobacterium bifidus, Bifidobacterium breve, Bifidobacterium infantis, Bifidobacterium adolecentis, Bifidobacterium lactis, Enterococcus faeciurn*, and combinations thereof.

In some embodiments, the probiotic composition includes one or more biosurfactant-producing microorganisms, one or more antiadhesion-producing microorganisms, and one or more bio-film producing microorganisms. In some embodiments, the species of biosurfactant-producing microorganism, antiadhesion-producing microorganism, and biofilm-producing microorganism are selected and included in specific concentrations according to their use for food product contact surfaces in food processing facilities.

In some embodiments, the probiotic composition includes one or more biosurfactant-producing microorganisms. Generally, a biosurfactant is an amphiphilic material, i.e. lipid or a derivative thereof, present in a living body which includes a hydrophilic moiety and a hydrophobic moiety in a single molecule. Generally, biosurfactant is used as a comprehensive term including all surfactants derived from living organisms. Herein, where specified, the biosurfactant in association with the term biosurfactant-producing microorganism, refers to one or more surfactants produced by microorganisms. Certain biosurfactants may have lower toxicity and higher biodegradability than conventional synthetic surfactants. Biosurfactants can be used for highly specific purposes due to their complex chemical structures and they are not easily synthesized by conventional methods. Additionally, biosurfactants are very useful since they have similar physical and chemical effects to chemically synthesized surfactants such as surface tension reduction and temperature and pH stability enhancement.

While the at least one biosurfactant-producing microorganism may be any microorganism or microbe known to produce biosurfactants, in particular embodiments disclosed herein, the at least one biosurfactant-producing microorganism is from the genus *Lactobacillus*, for example, they may be selected from human or animal hosts and mixtures thereof. In some embodiments the at least one biosurfactant-producing microorganism may be selected from the following: *Lactobacillus acidophilus, Lactobacillus casei, Lactobacillus paracasei, Lactobacillus fermentum, Lactobacillus lactis, Lactobacillus reuterii, Lactobacillus rhamnoses, Lactobacillus bulgaricus, Lactobacillus plantarum, Lactobacillus salivarius, Lactobacillus delbrueckii, Lactobacillus Lactobacillus helveticus, Lactobacillus salivarius, Lactobacillus brevis, Lactobacillus sakei, Lactobacillus johnsonii, Bifidobacterium longum, Bifidobacterium bifidum, Bifidobacterium breve, Bifidobacterium infantis, Bifidobacterium adolecentis, Bifidobacterium lactis, Bidobacterium animalis, Enterococcus faecium*, and combinations thereof.

In some embodiments, the biosurfactant-producing microorganism may be a strain of microorganisms known to produce biosurfactants in improved yields. For example, many species of *Bacillus* produce biosurfactants, however, *Bacillus sublilis* and *Bacillus licheniformis* are known to produce significant quantities of biosurfactants. Furthermore, specific strains of *Bacillus subtilis* are known to produce improved yields of biosurfactants such as *B. subtilis* ATCC 2133 1, *B. subtilis* ATCC 21332, *B. subtilis* SD901 (FERM BP.7666), *B. Subitilis* NRRL B-3383 and *B. subtilis* RSA-203 or mixtures thereof. Many strains of biosurfactant-producing microorganisms may be commercially or publicly available. In some embodiments, the at least one biosurfactant-producing microorganism is *B. subtilis* strain RSA-203. RSA-203 is a microorganism that is a strain of *Bacillus subtilis*. It is a rod-shaped, aerobic, Gram-positive, β-hemolytic microbe capable of forming endospores.

In some embodiments, the probiotic composition comprises from about $10^3$ to $10^{15}$ colony forming units ("CFUs") of the biosurfactant-producing microorganism per gram of finished product. In some embodiments, the probiotic composition comprises from about $10^4$ to about $10^{14}$ CFUs of the biosurfactant-producing microorganism per gram of finished product. In some embodiments, the probiotic composition comprise from about $10^5$ to about $10^{15}$ CFUs of biosurfactant-producing microorganism per gram of finished product. In some embodiments, the probiotic composition comprises from about $10^6$ to $10^{11}$ colony forming units of the biosurfactant-producing microorganism per gram of finished product. In some embodiments, the probiotic composition comprises from about $10^2$ to about $10^5$ colony forming units of the biosurfactant-producing microorganism per gram of finished product.

In some embodiments, the probiotic composition comprises a mixture of suitable biosurfactant-producing microorganisms. In these embodiments, where the at least one biosurfactant-producing microorganism contains a mixture of microorganisms, the ratio and/or amounts of each included microorganism may be adjusted to determine the overall amount of biosurfactant produced. In some embodiments, the biosurfactant-producing microorganism contains a mixture of microorganisms, the ratio and/or amounts of each included microorganism may be adjusted to produce a desired biosurfactant profile including certain amounts of different biosurfactant produced.

Without being bound by any particular theory, in certain embodiments the biosurfactant-producing microorganism may dispose a biosurfactant on the pathogenic biofilm of the food product contact surface and the biosurfactant may act to remove unforeseen pathogenic biofilms that cannot be reached by detergents or other chemical surfactants that are in forms such as foams, wetting agents, water, acids, bases, or other oxidizing chemicals.

In some embodiments, where the probiotic composition includes at least one biosurfactant-producing microorganism, the biosurfactant produced by the microorganism may alter the surface tension of the pathogenic biofilm existing on a surface to which the biosurfactant-producing microorganism is applied. As such, the biosurfactant produced by the biosurfactant-producing microorganism allows for the dispersion of built-up pathogenic biofilm existing on the applied surface, which may be a food product contact surface. Furthermore, without being bound by any particular theory, application of the at least one biosurfactant-producing microorganism that alters the surface tension of the pathogenic biofilm promotes wetting at the surface of the pathogenic biofilm, thus allowing for dispersion of the pathogenic biofilm. Additionally, the biosurfactant-producing microorganism that acts to change the surface tension of the pathogenic biofilm may prevent additional pathogen adherence to the surface of the biofilm, while dispersing the pathogenic biofilm from the surface, i.e. a food product contact surface.

In certain embodiments, the probiotic composition includes at least one antiadhesion-producing microorganism. While the at least one antiadhesion-producing microorganism may be any microorganism or microbe known to produce an antiadhesion composition, such as an exopolysaccharide, in some embodiments disclosed herein, the at least one antiadhesion-producing microorganism is selected from *Bifidobacterium longum, Bifidobacterium bifidum, Bifidobacterium breve, Bifidobacterium infantis, Bifidobacterium adolecentis, Bifidobacterium lactis, Bidobacterium animalis, Lactobacillus acidophilus, Lactobacillus casei, Lactobacillus paracasei, Lactobacillus fermentum, Lactobacillus lactis, Lactobacillus reuterii, Lactobacillus rham-* noses, *Lactobacillus bulgaricus, Lactobacillus plantarum, Lactobacillus salivarius, Lactobacillus delbrueckii, Lactobacillus helveticus, Lactobacillus brevis, Lactobacillus sakei, Lactobacillus johnsonii*, and combinations thereof.

In certain embodiments, the antiadhesion-producing microorganism may be one that produces increased amounts of an antiadhesion substance, such as an exopolysaccharide, in comparison with other antiadhesion-producing microorganisms.

In some embodiments, the probiotic composition comprises from about $10^3$ to $10^{15}$ colony forming units ("CFUs") of the antiadhesion-producing microorganism per gram of finished product. In some embodiments, the probiotic composition comprises from about $10^4$ to about $10^{14}$ CFUs of the antiadhesion-producing microorganism per gram of finished product. In some embodiments, the probiotic composition comprise from about $10^5$ to about $10^{15}$ CFUs of antiadhesion-producing microorganism per gram of finished product. In some embodiments, the probiotic composition comprises from about $10^6$ to $10^{11}$ colony forming units of the antiadhesion-producing microorganism per gram of finished product. In some embodiments, the probiotic composition comprises from about $10^2$ to about $10^5$ colony forming units of the antiadhesion-producing microorganism per gram of finished product.

In some embodiments, the antiadhesion-producing microorganism comprises a mixture of suitable antiadhesion-producing microorganisms. In these embodiments, where the antiadhesion-producing microorganism contains a mixture of microorganisms, the ratio and/or amounts of each included microorganism may be adjusted to determine the overall amount of antiadhesion material produced. In some embodiments where the antiadhesion-producing microorganism contains a mixture of microorganisms, the ratio and/or amounts of each included microorganism may be adjusted to produce a desired antiadhesion composition profile including certain amounts of antiadhesion compositions having different physical and chemical properties.

Without being bound by any particular theory, in some embodiments the antiadhesion-producing microorganism acts to prevent the pathogen from producing cellular factors that promote the pathogens adherence on a surface, such as a food product contact surface. For example, in some embodiments, the antiadhesion-producing microorganism may act to downregulate genetic expression of adhesion molecules produced by the pathogen.

Thus, without being bound by any particular theory, in certain embodiments where the probiotic composition comprises both a biosurfactant-producing microorganism and an antiadhesion-producing microorganism, the antiadhesion-producing microorganism prevents the existing pathogen from producing adhesion factors in the biofilm while the biosurfactant-producing composition begins to mitigate and disperse the existing pathogenic biofilm.

In certain embodiments, the probiotic composition includes one or more biofilm-producing microorganisms. In some embodiments, the probiotic composition comprises a biofilm-producing microorganism that is a primary biofilm-producing microorganism, i.e. one that is capable of forming a biofilm that adheres to clean surfaces. In some embodiments, the probiotic composition comprises a biofilm-producing microorganism that is a secondary biofilm-producing microorganism, i.e. one that produces a biofilm capable of adhering to other biofilms, such as those produced by the primary biofilm-producing microorganism or those produced by pathogenic organisms. As such, in some embodiments, the probiotic composition comprises one or more primary biofilm-forming microorganisms and one or more secondary biofilm-forming microorganisms.

In some embodiments, the biofilm-producing microorganism may be selected such that it is the same microorganism as the biosurfactant-producing microorganism or the bioadhesion-producing microorganism.

While the at least one biofilm-producing microorganism may be any microorganism or microbe known to produce biofilm, in some embodiments disclosed herein, the at least one biofilm-producing microorganism is selected from the following: *Bifidobacterium longum, Bifidobacterium bifidum, Bifidobacterium breve, Bifidobacterium infantis, Bifidobacterium adolecentis, Bifidobacterium lactis, Bidobacterium animalis, Lactobacillus acidophilus, Lactobacillus casei, Lactobacillus paracasei, Lactobacillus fermentum, Lactobacillus lactis, Lactobacillus reuterii, Lactobacillus rhamnoses, Lactobacillus bulgaricus, Lactobacillus plantarum, Lactobacillus salivarius, Lactobacillus delbrueckii, Lactobacillus Lactobacillus helveticus, Lactobacillus salivarius, Lactobacillus brevis, Lactobacillus sakei, Lactobacillus johnsonii*, and combinations thereof. In certain embodiments, the biofilm-producing microorganism may be one that produced increased amounts of biofilm in comparison with other biofilm-producing microorganisms.

In some embodiments, the probiotic composition comprises from about $10^3$ to $10^{15}$ colony forming units ("CFUs") of the biofilm-producing microorganism per gram of finished product. In some embodiments, the probiotic composition comprises from about $10^4$ to about $10^{14}$ CFUs of the biofilm-producing microorganism per gram of finished product. In some embodiments, the probiotic composition comprise from about $10^5$ to about $10^{15}$ CFUs of biofilm-producing microorganism per gram of finished product. In some embodiments, the probiotic composition comprises from about $10^6$ to $10^{11}$ colony forming units of the biofilm-producing microorganism per gram of finished product. In some embodiments, the probiotic composition comprises from about $10^2$ to about $10^5$ colony forming units of the biofilm-producing microorganism per gram of finished product.

In some embodiments, the biofilm-producing microorganism comprises a mixture of suitable biofilm-producing microorganisms. In these embodiments, where the biofilm-producing microorganism contains a mixture of microorganisms, the ratio and/or amounts of each of the included microorganisms may be adjusted to determine the overall amount of biofilm produced. In some embodiments where the biofilm-producing microorganism contains a mixture of microorganisms, the ratio and/or amounts of each included microorganism may be adjusted to produce a desired biofilm profile including certain amounts of biofilms having different physical and chemical properties.

In some embodiments, the selected biosurfactant-producing microorganism may be capable of producing an antiadhesion substance and thus, is also an antiadhesion-producing microorganism. In some embodiments, the biofilm-producing microorganism may be capable of producing an antiadhesion substance and thus, is also an antiadhesion-producing microorganism. Indeed, in some embodiments a microorganism is selected that is capable of being the biosurfactant-producing microorganism, the antiadhesion-producing microorganism, and/or the biofilm-producing microorganism.

In certain embodiments the biosurfactant-producing microorganism, antiadhesion-producing microorganism, and the biofilm-producing organism may all commensally exist on the food product surface thereby preventing any further infection from harmful pathogens. For example, in example embodiments where the probiotic composition is applied to a food product contact surface, the biosurfactant-producing microorganism, bioadhesion-producing microorganism, and biofilm-producing microorganism may be applied simultaneously to the food surface and each are capable of surviving and exerting certain effects on the pathogenic biofilm and associated pathogens thereon. Indeed, application of the probiotic composition disclosed herein, allows for both mitigation of the pathogenic biofilm and mitigation of the pathogen via suitable mechanisms.

In some embodiments, the probiotic composition comprises *Lactobacillus acidophilus*, and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus acidophilus*, and at least two microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus acidophilus*, and at least three microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus acidophilus*, *Enterococcus faecium*, and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus acidophilus*, *Enterococcus faecium*, and at least two microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus acidophilus*, *Enterococcus faecium*, and at least three microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus casei* and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus casei* and at least two microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus paracasei* and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus paracasei* and at least two microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus paracasei* and at least three microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus fermentum* and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus fermentum* and at least two microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus fermentum* and at least three microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus lactis* and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus lactis* and at least two microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus lactis* and at least two microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus reuterii* and at least one microorganism selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus reuterii* and at least two microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*. In some embodiments, the probiotic composition comprises *Lactobacillus reuterii* and at least three microorganisms selected from the following *Bifidobacterium longum*, *Bifidobacterium bifidum*, *Bifidobacterium breve*, *Bifidobacterium infantis*, *Bifidobacterium adolecentis*, *Bifidobacterium lactis*, and *Bidobacterium animalis*.

In some embodiments, the probiotic composition comprises *Lactobacillus rhamnoses* and at least one microorganism selected from the following *Bifidobacterium longum*, *Bifidobacterium bifidum*, *Bifidobacterium breve*,

*Bifidobacterium infantis, Bifidobacterium adolecentis, Bifidobacterium lactis*, and *Bidobacterium animalis*. In some embodiments, the probiotic composition comprises *Lactobacillus* rhamnoses and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus* rhamnoses and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus bulgaricus* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus bulgaricus* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus bulgaricus* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus plantarum* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus plantarum* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus plantarum* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus salivarius* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus salivarius* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus salivarius* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus delbrueckii* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus delbrueckii* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus delbrueckii* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus helveticus* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus helveticus* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus helveticus* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus brevis* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus brevis* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus brevis* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus sakei* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus sakei* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium ani-*

*malis*. In some embodiments, the probiotic composition comprises *Lactobacillus sakei* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition comprises *Lactobacillus johnsonii* and at least one microorganism selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus johnsonii* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*. In some embodiments, the probiotic composition comprises *Lactobacillus johnsonii* and at least three microorganisms selected from the following *Bifidobacterium longum, Bifidobacterium bifidum, Bifidobacterium breve, Bifidobacterium infantis, Bifidobacterium adolecentis, Bifidobacterium lactis*, and *Bidobacterium animalis*.

In some embodiments, the probiotic composition may further include one or more prebiotics. In some embodiments, the probiotic composition may include prebiotic material.

In some embodiments, the probiotic composition may include any suitable fillers or other ingredients such as nonfat dry milk, maltodextrin, corn starch, asparagus powder, rice flour, chicory powder, artichoke powder, butternut squash powder, carrot powder, pumpkin powder, sweet potato powder, beet powder, garlic powder, onion powder, leek powder, potato powder, pea powder, barley flour, soy powder, silicate powder, silica powder, and combinations thereof. In certain embodiments, the probiotic composition may include only selected microorganisms and other ingredients that have been approved by the United States Food and Drug Administration ("USFDA" or "FDA") and are Generally Recognized as Safe ("GRAS"). Accordingly, in embodiments where the probiotic composition is formulated to only include GRAS ingredients, the probiotic composition may be most suited for food product contact surfaces on food manufacturing equipment, given that the probiotic composition will not contaminate the food product being produced.

In some embodiments, the probiotic composition(s) disclosed herein may be in any form known in the art. For example, the probiotic composition may be in liquid or powdered form.

In some embodiments, the probiotic composition may be provided in an aerosol form. Generally, aerosol dispensers have been commonly used to dispense personal, household, industrial, and medical products, and to provide a low cost, easy to use method of dispensing a powdered and/or liquid product. Typically, aerosol dispensers include a container, which contains a product to be dispensed. A propellant is used to discharge the product from the container. Accordingly, in some embodiments, the probiotic composition may be in an aerosol form, capable of being dispensed from any suitable aerosol container known in the art.

Indeed, in certain methods disclosed herein, dispensing the probiotic composition in aerosol form may provide additional benefits not previously contemplated. For example, in the food producing industry, the equipment used to produce certain food products may include equipment mounted vertically, equipment mounted high over the factory floor, and/or equipment including joints, cracks, or crevices having certain geometries that make it nearly if not all but impossible for traditional cleaning and sanitizing solutions to reach. Accordingly, providing the probiotic composition in aerosol form allows for multi-directional application of the probiotic composition on the desired surface.

In some embodiments, the probiotic composition may be formulated as a dry, powder blend composition. In these embodiments, the dry blend powder including the probiotic composition disclosed herein can easily move with or without air currents and be distributed to surfaces in the food processing environment that cannot be easily accessed, reached, cleaned, or sanitized. In certain embodiments, the probiotic composition is a dry blend powder that is ready to use without any additional mixing, agitation, foaming, or liquefying. In certain embodiments, the dry blend powder probiotic composition can be used without any water, alcohol, or other chemical solution for distribution. In some embodiments, the dry blend powder including the probiotic composition disclosed herein may be hand distributed to the desired surface or may be distributed with any suitable air displacement system, gravity feed system, or mass delivery system.

In some embodiments described herein, the probiotic composition is produced and manufactured in compliance with current Good Manufacturing Practice as specified in 21 C.F.R. § 110.

In some embodiments, provided herein are methods for reducing contamination of food processing facilities by applying the probiotic composition disclosed herein to a desired surface. In some embodiments, the surface to which the probiotic composition is applied is a food product contact surface.

In some embodiments, provided herein are methods for mitigating and/or dispersing pathogenic biofilm on a surface by applying the probiotic composition disclosed herein to the surface. In certain embodiments, the surface is a food product contact surface.

In some embodiments, provided herein are methods for inducing the competitive inhibition of pathogens on the surface of a food processing facility by disposing the probiotic composition disclosed herein to a surface. In some embodiments, the surface to which the probiotic composition is applied is a food product contact surface.

In some embodiments, provided herein are methods for inducing the competitive exclusion of pathogens on the surface of a food processing facility by disposing the probiotic composition disclosed herein to a surface. In some embodiments, the surface to which the probiotic composition is applied is a food product contact surface.

In some embodiments, the methods herein comprise the step of applying or disposing the probiotic composition on a food product contact surface having a pathogenic biofilm thereon to mitigate and/or disperse the pathogenic biofilm. Indeed, application of the probiotic composition as disclosed herein provides for the removal of pathogenic biofilms from surfaces, including hard, if not impossible, to reach food product surfaces in a food production facility.

In some embodiments, the methods herein comprise the step of disposing the probiotic composition on a food contact surface to inhibit or exclude the growth and colonization of certain pathogens. Indeed, the application of the probiotic composition as disclosed may provide competitive inhibition of certain pathogens present on the food contact surface. In some embodiments, application of the probiotic composition on the food product contact surface may competitively exclude pathogens.

In some embodiments, the disclosure is directed to a method of cleaning, sanitizing, and controlling the microorganism colony on a food product contact surface by disposing the probiotic composition disclosed herein on the food product contact surface. Indeed, application of the probiotic composition disclosed herein, is capable of penetrating impossible to reach surfaces, mitigating pathogenic biofilm on the surface, dispersing pathogenic biofilm on the surface to create a clean surface, and/or colonizing the surface with probiotics and not pathogens.

Further, in certain food processing equipment that remains mostly closed to the external environment, application of the probiotic composition may inhibit or exclude the growth of harmful pathogens and repopulate the food product contact surface with the microorganisms present in the probiotic composition. Indeed, in certain embodiments, the probiotic composition is formulated to include a biosurfactant-producing probiotic in combination with an antiadhesion-producing microorganism and a bio-film producing microorganism. In these embodiments, without being bound by any particular theory, the biosurfactant-producing organism is capable of penetrating and/or breaking-down the biofilm that exists or is being produced by pathogens on the food product surface. The antiadhesion-producing microorganism is capable of altering the existing pathogens ability to continue to produce biofilm. While, the biofilm-producing organism may adhere to the food product contact surface and establish a new beneficial microorganism ecosystem on the food product surface. As such, in certain embodiments the subsequent biofilm formation provided by the biofilm-forming microorganism in the probiotic composition may attach or adhere itself to the food product contact surface. As such, the probiotic composition including the biosurfactant-producing microorganism, antiadhesion-producing microorganism, and biofilm-producing microorganism provides a biofilm control strategy by removing the biofilm and replacing and/or inhibiting the growth of certain pathogenic microorganisms on the food product contact surfaces of food manufacturing equipment.

In certain embodiments, the methods disclosed herein may be one-step methods, that step being the application of the probiotic composition as disclosed herein on the food product contact surface. Indeed, the probiotic composition disclosed herein is capable both of mitigating any existing biofilm on the food product surface and competitively excluding pathogens existing on the food product contact surface. As such, application of the probiotic composition disclosed herein eliminates the need to pretreat the desired surface with a detergent or surfactant prior to sanitizing the desired surface. As such, in certain embodiments disclosed herein, the methods disclosed do not require the application of a detergent or surfactant to the desired surface, i.e. food product contact surface, before application of any probiotics.

Further, after application of the probiotic composition disclosed herein, the probiotic composition may develop its own biofilm and colonize the food product contact surface to which it is applied. The adherence and colonization of the probiotic composition disclosed herein may further prevent or inhibit pathogens from re-establishing on the food product surface. Accordingly, in certain embodiments, application and use of the probiotic composition(s) disclosed herein allows for control of the microorganism biofilm on a desired surface, such as a food product contact surface. Such control would further eliminate the need for additional or multiple sanitization procedures, which, could provide substantial economic benefits to the food production industry. For example, use of the probiotic composition(s) as disclosed herein, would eliminate the need to purchase additional detergents or sanitization chemicals and would also prevent food production facilities from being forced to shut-down production equipment for multiple cleanings.

Accordingly, in some examples, the application of the probiotic composition disclosed herein allows for the remediation and exclusion of pathogens from the surface to which it is applied. Further, the application of the probiotic composition disclosed herein to a desired surface allows for the adherence and colonization of non-toxic and GRAS microorganisms. As such, the probiotic composition disclosed herein may be applied to food product contact surfaces without worry that the ingredients will contaminate the food product.

Further, disclosed in some embodiments, are methods for controlling the microorganism biofilm on a food product contact surface via disposing the probiotic composition disclosed herein on the food product contact surface. Further, in embodiments where the probiotic composition includes all GRAS ingredients, the food production facility will no longer need to continue to wash or rinse off food contact surfaces, as the food product being produced may safely come into contact with the GRAS ingredients comprising the probiotic composition disclosed herein.

Without being bound by any particular theory, in some embodiments, the probiotic composition may remove and replace pathogens from a biofilm on a food product contact surface via a blanketing mechanism. Indeed, the probiotic composition disclosed herein may populate the food product contact surface and prevent the pathogen from further bonding to and populating space on the food product contact surface.

In some embodiments, the probiotic composition may provide initial inhibition of pathogenic bacteria on the food product contact surface by excreting certain antiadhesion compositions that may change the molecular charge and/or the hydrophobicity of the food product contact surface thereby preventing further pathogen binding to the food product contact surface.

In some embodiments, the probiotic composition includes one or more antiadhesion-producing microorganisms which may, when applied to the food product contact surface, change the surface tension of any pathogenic biofilm existing thereon, which allows for the dispersion of built-up pathogenic biofilm existing on the food product surface. Further, the one or more antiadhesion producing microorganisms may further prevent the pathogens from secreting their own biofilm. For example, in certain embodiments, the antiadhesion-producing microorganism may produce one or more exopolysaccharides. Without being bound by any particular theory, the exopolysaccharides may down regulate genetic expression in a pathogen, thus preventing the pathogen from producing adherence promoting compounds and/or biofilm. Furthermore, in embodiments where the probiotic includes an antiadhesion-producing microorganism, the exopolysaccharide secreted by the antiadhesion-producing microorganism may further assist the formation of the probiotic composition's formation of biofilm on the food product contact surface.

In certain embodiments, and without being bound by any particular theory, the probiotic composition disclosed herein may interfere with the quorum sensing mechanism of the pathogen, thus interfering with and inhibiting the pathogen from producing biofilm.

Without being bound by any particular theory, in some embodiments, the probiotic composition disclosed herein may contribute to the breakdown of the matrix of the pathogenic biofilm via degrading the protein, carbohydrate, and nucleic acid structure of the pathogen biofilm.

In some embodiments, the disclosure is directed to a method of removing a pathogen from a food product contact surface via applying an aerosolized form of the probiotic composition disclosed herein to the food product contact surface. Indeed, in certain embodiments the pathogen may exists in its biofilm on the food product contact surface. Further, the aerosolized application of the probiotic composition to the food product contact surface ensures multidirectional delivery of the probiotic composition to the food product contact surface. As such, in certain embodiments, disclosed are methods of applying a probiotic composition to a hard to reach food product contact surface, such as a nook or curve in the food product production equipment that may not be reachable or is capable of being exposed via liquid applications.

EXAMPLES

The Examples below illustrate the use of a probiotic composition in accordance with the disclosure herein to remediate *Salmonella* in a food product facility.

Example 1

Two different containers were used that represent potential contact surfaces or food product contact surfaces. One container used was a 304 stainless steel 1.5 L container with a diameter of 12.4 cm and height of 15.9 cm (represented in Tables 1-3 and FIG. 1 herein as 304 SS). The other food container was a food grade plastic container having a diameter of 12.4 cm and a height of 17.8 cm.

To form the pathogenic biofilm on the containers, *Salmonella infantis* was grown in Tryptic Soy Broth at 35° C. for 24 hrs and sub-cultured two times more on consecutive days. The cells were prepared by centrifugation at 4000 rpm for 10 min. The pellet, obtained after centrifugation, was re-suspended in 0.1% Buffered Peptone Water. Serial dilution (10-fold) was used to prepare the concentrations (CFU/ml) of the *Salmonella* solution. One mL of the appropriate concentration of the *Salmonella* solution was applied evenly to each container with sterile pipets. The 1 mL of *Salmonella* solution was distributed over a 2-3 hour time period in each container with agitation. Once the entire 1 mL *Salmonella* solution was delivered evenly over the surface of the container, the container with the *Salmonella* was dried overnight at 70° F. in a closed container.

Control and treated samples were prepared by adding an equal amount of the dry formula, having a starch based, either with or without the probiotic. The total amount of dry product dusted on the inside surface of each container was 3.8 grams of a concentration of $1.6\times10^{10}$ CFU/g of both the *Lactobacillus* spp. and the *Bifidobacterium* spp or 3.8 grams of a control powder containing no *Lactobacillus* or *Bifidobacterium*. This application was left overnight at 70° F. in a closed container.

A total of 454 g of a dry, sterile, hard food pellet was added to the containers 15 hours after dry powder application. The food pellet and the interaction with the food contact surface attempts to mimic food passing through a production line that has a pathogenic biofilm and has had the probiotic added to the surface. The food pellets were mixed for 10 min at 10 rpm on a rotating wheel. After 10 minutes, the entire 454 g of food was transferred to 4× the amount (1/5 dilution) of Buffered Peptone Water (BPW) and enriched at 37° C. for 22 hrs. A secondary enrichment in 5 ml pre-warmed Brain Heart Infusion (BHI) broth was inoculated with 0.1 ml of the BPW enriched sample and incubated for 3 hrs at 37° C. The samples were tested for *Salmonella* by immunological method (AOAC030301) and DNA-PCR method (AOAC100201).

Each day, after sampling as above, another 3.8 of either the control or probiotic dry powder was added to each container to monitor the removal of the *Salmonella* over time (days) by the probiotic.

Testing was stopped after the *Salmonella* could not be detected by the above sampling and testing for 3 consecutive days.

The experimental procedure was repeated in triplicate. Tables 1-3 represent the three replications of the described procedure performed on different days. Furthermore, a graphical illustration of the results of the replications of Example 1 are shown in FIG. 1.

Table 1. Results from Example 1, first replication showing exclusion of *Salmonella*.

TABLE 1

| *Salmonella* Inoculum $1.3\times10^3$ CFU/mL (one milliliter into each container) and 3.5 g of powder (probiotic or starch) | | | | |
|---|---|---|---|---|
| Day | Plastic Control (Starch) | Plastic Test (Probiotics) | Metallic Control (Starch) | Metallic Test (Probiotics) |
| 0 | Positive | Positive | Positive | Positive |
| 1 | Positive | Positive | Positive | Positive |
| 2 | Positive | Positive | Positive | Negative |
| 3 | Positive | Negative | Positive | Positive |
| 4 | Positive | Positive | Positive | Negative |
| 5 | Positive | Negative | Positive | Negative |
| 6 | Positive | Negative | Negative | Negative |
| 7 | Positive | Negative | Negative | Negative |
| 8 | Negative | Negative | Negative | Negative |
| 9 | Positive | Negative | Negative | Negative |
| 10 | Negative | Negative | Negative | Negative |
| 11 | Negative | Negative | Negative | Negative |
| 12 | Negative | Negative | Negative | Negative |

Table 2. Results from Example 1, second replication showing exclusion of *Salmonella*.

TABLE 2

| *Salmonella* Inoculum $1.4\times10^3$ CFU/mL (one milliliter into each container) and 3.5 g of powder (probiotic or starch) | | | | |
|---|---|---|---|---|
| Day | Plastic Control (Starch) | Plastic Test (Probiotics) | Metallic Control (Starch) | Metallic Test (Probiotics) |
| 0 | Positive | Positive | Positive | Positive |
| 1 | Positive | Positive | Positive | Negative |
| 2 | Positive | Negative | Positive | Positive |
| 3 | Positive | Positive | Positive | Negative |
| 4 | Positive | Negative | Negative | Negative |
| 5 | Positive | Negative | Positive | Negative |
| 6 | Negative | Negative | Positive | Negative |
| 7 | Positive | Negative | Negative | Negative |
| 8 | Positive | Negative | Negative | Negative |
| 9 | Positive | Negative | Negative | Negative |
| 10 | Negative | Negative | Negative | Negative |
| 11 | Negative | Negative | Negative | Negative |
| 12 | Negative | Negative | Negative | Negative |

Table 3. Results from Example 1, third replication showing exclusion of *Salmonella*.

TABLE 3

Salmonella Inoculum 1.2 × 10³ CFU/mL (one milliliter into each container) and 3.5 g of powder (probiotic or starch)

| Day | Plastic Control (Starch) | Plastic Test (Probiotics) | Metallic Control (Starch) | Metallic Test (Probiotics) |
| --- | --- | --- | --- | --- |
| 0 | Positive | Positive | Positive | Positive |
| 1 | Positive | Positive | Positive | Positive |
| 2 | Positive | Positive | Positive | Negative |
| 3 | Positive | Positive | Positive | Positive |
| 4 | Positive | Negative | Positive | Negative |
| 5 | Positive | Negative | Positive | Negative |
| 6 | Positive | Negative | Negative | Negative |
| 7 | Negative | Negative | Negative | Negative |
| 8 | Positive | Negative | Negative | Negative |
| 9 | Positive | Negative | Negative | Negative |
| 10 | Negative | Negative | Negative | Negative |
| 11 | Negative | Negative | Negative | Negative |
| 12 | Negative | Negative | Negative | Negative |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A method of treating a surface of a food processing facility to remove pathogenic biofilm and inhibit the growth of a pathogen thereon, the method comprising the step of:
    disposing a probiotic composition onto the surface of the food processing facility, wherein the probiotic composition comprises at least one biosurfactant-producing microorganism and at least one antiadhesion-producing microorganism, wherein the probiotic composition comprises at least $10^9$ CFUs of probiotic to about $10^{15}$ CFUs of probiotic per gram of composition,
    wherein the at least one biosurfactant-producing microorganism and at least one antiadhesion-producing microorganism remove pathogenic biofilm from the surface.

2. The method of claim 1, wherein the biosurfactant-producing microorganism is selected from the group consisting of Lactobacillus acidophilus, Lactobacillus casei, Lactobacillus paracasei, Lactobacillus fermentum, Lactobacillus lactis, Lactobacillus reuteri, Lactobacillus rhamnosus, Lactobacillus bulgaricus, Lactobacillus plantarum, Lactobacillus salivarius, Lactobacillus delbrueckii, Lactobacillus helveticus, Lactobacillus brevis, Lactobacillus sakei, Lactobacillus johnsonii, Bifidobacterium longum, Bifidobacterium bifidum, Bifidobacterium breve, Bifidobacterium infantis, Bifidobacterium adolescentis, Bifidobacterium lactis, Bidobacterium animalis, Enterococcus faecium, and combinations thereof.

3. The method of claim 1, wherein the at least one antiadhesion-producing microorganism is selected from the group consisting of Lactobacillus acidophilus, Lactobacillus casei, Lactobacillus paracasei, Lactobacillus fermentum, Lactobacillus lactis, Lactobacillus reuterii, Lactobacillus rhamnoses, Lactobacillus bulgaricus, Lactobacillus plantarum, Lactobacillus salivarius, Lactobacillus delbrueckii, Lactobacillus Lactobacillus helveticus, Lactobacillus brevis, Lactobacillus sakei, Lactobacillus johnsonii, Bifidobacterium longum, Bifidobacterium bifidum, Bifidobacterium breve, Bifidobacterium infantis, Bifidobacterium adolescentis, Bifidobacterium lactis, Bidobacterium animalis, Enterococcus faecium, and combinations thereof.

4. The method of claim 1, wherein the pathogen is Salmonella.

5. The method of claim 1, wherein the surface of the food processing facility is a food product contact surface.

6. The method of claim 1, wherein the biosurfactant-producing microorganism is present in an amount of from $10^3$ to $10^{15}$ colony forming units per gram of the probiotic composition and wherein the antiadhesion-producing microorganism is present in an amount of from $10^3$ to $10^{15}$ colony forming units per gram of the probiotic composition.

7. The method of claim 1, wherein the at least one biosurfactant-producing microorganism is certified generally recognized as safe (GRAS) and, wherein the at least one antiadhesion-producing microorganism is generally recognized as safe (GRAS).

8. The method of claim 1, wherein the probiotic composition is in aerosol form.

9. The method of claim 1, wherein the probiotic composition further comprises a biofilm-producing microorganism.

10. The method of claim 9, wherein the biofilm-producing microorganism is present in an amount of from $10^3$ to $10^{15}$ colony forming units per gram of the probiotic composition.

11. The method of claim 1, wherein the pathogen is Listeria.

12. The method of claim 1, wherein the probiotic composition is a powder.

13. A method for mitigating pathogenic biofilm and inhibiting pathogen growth on a food product contact surface, the method comprising the step of applying a probiotic composition comprising at least one biosurfactant-producing microorganism and at least one antiadhesion-producing microorganism to the food product contact surface, wherein the probiotic composition comprises at least $10^9$ CFUs of probiotic to about $10^{15}$ CFUs of probiotic per gram of composition.

14. The method of claim 13, wherein the probiotic composition is in aerosol form.

15. The method of claim 13, wherein the pathogen is Salmonella.

16. The method of claim 13, wherein the pathogen is Listeria.

17. The method of claim 13, wherein the probiotic composition is a powder.

* * * * *